United States Patent [19]

Wei et al.

[11] Patent Number: 5,723,311

[45] Date of Patent: Mar. 3, 1998

[54] HUMAN DNA TOPOISOMERASE I α

[75] Inventors: Ying-Fei Wei, Darnestown; Mark D. Adams, North Potomac; Robert D. Fleischmann, Gaithersburg, all of Md.

[73] Assignee: Human Genome Sciences, Inc., Rockville, Md.

[21] Appl. No.: 458,477

[22] Filed: Jun. 2, 1995

Related U.S. Application Data

[63] Continuation-in-part of PCT/US94/05701, May 18, 1994.

[51] Int. Cl.⁶ .................. C12P 21/02; C12N 15/12; C12N 9/90

[52] U.S. Cl. .............. 435/69.1; 435/172.3; 435/233; 435/320.1; 536/23.2; 536/23.5

[58] Field of Search .................... 435/233, 69.1, 435/320.1, 172.3; 536/23.2, 23.5

[56] References Cited

PUBLICATIONS

Wetmore et al. Human lung expresses unique gamma--glutamyl transpeptidase transcripts Proc. Natl. Acad. Sci. U.S.A. vol. 90 7461–7465, 1993.

Voojis et al. Libraries for each human chromosome, constructed from sorter-enriched chromosomes by using linker-adaptor PCR Am. J. Human Genetics vol. 52 586–597, 1993.

*Primary Examiner*—James Ketter
*Assistant Examiner*—John S. Brusca
*Attorney, Agent, or Firm*—Elliott M. Olstein; J. G. Mullins

[57] ABSTRACT

Disclosed is a human is a hTopI-α polypeptide and DNA (RNA) encoding such hTopI-α polypeptide. Also provided is a procedure for producing such polypeptide by recombinant techniques and antibodies and antagonists against such polypeptide. Also provided are methods of using the antibodies and antagonist inhibitors to inhibit the action of hTopI-α for therapeutic purposes such as an antitumor agent, to detect an autoimmune disease, or retroviral infections and to treat adenocarcinoma of the colon. Diagnostic methods for detecting mutations in the coding sequence and alterations in the concentration of the polypeptides in a sample derived from a host are also disclosed.

19 Claims, 11 Drawing Sheets

FIG. 1A

```
          20                    40
GCAGATGCGGCGTGGTGCGGCTGCTGCGGCTCCGGGCTGCTGACGCTCGGGAGGT
------+---------+---------+---------+---------+---------+
CGTCTACGCCGCACCACGCCGACGACGCCGAGGCCCGACGACTGCGAGCCCTCCA
       M  R  V  V  R  L  L  R  L  R  A  A  L  T  L  L  G  E  V
                         60                       80                   100

CCCCCGCCGCCCGGCCCTCCCGGGTGTCCCGGGCTCGGCAGGACGCAGAAGGGCAGTGG
------+---------+---------+---------+---------+---------+
GGGGGCGGCGGGCCGGGAGGGCCCACAGGGCCCGAGCCGTCCTGCGTCTTCCCGTCACC
   P  R  R  P  A  S  R  G  V  P  G  S  R  R  T  Q  K  G  S  G
        120                      140                     160

AGCCAGGTGGGAGAAGGAGAAGCACGAAGACGGGGGTGAAGTGGAGACAGCTGGAGCACAA
------+---------+---------+---------+---------+---------+
TCGGTCCACCCTCTTCCTCTTCGTGCTTCTGCCCCACTTCACCTCTGTCGACCTCGTGTT
   A  R  W  E  K  E  K  H  E  D  G  V  K  W  R  Q  L  E  H  K
        180                      200                     220
```

FIG. 1B

```
GGGCCCGTACTTCGCACCCCCATACGAGCCCCTTCCCGACGGAGTGCGTTTCTTCTATGA
---+---------+---------+---------+---------+---------+---------
CCCGGGCATGAAGCGTGGGGGTATGCTCGGGGAAGGGCTGCCTCACGCAAAGAAGATACT
 G  P  Y  F  A  P  P  Y  E  P  L  P  D  G  V  R  F  F  Y  E
240                      260                      280

AGGAAGGCCCTGTGAGATTGAGCGTGCCAGCGGAGGAGGTCCCCACTTTTTATGGAGGAT
---+---------+---------+---------+---------+---------+---------
TCCTTCCGGACACTCTAACTCGCACGGTCGCCTCCTCCAGGGGTGAAAAATACCCTCCTA
 G  R  P  V  R  L  S  V  P  A  E  E  V  P  T  F  Y  G  R  M
300                      320                      340

GTTAGATCATGAATACACAAAGGAGTTTCCGGAAGAACTTCTTCAATGACTGGCG
---+---------+---------+---------+---------+---------+---------
CAATCTAGTACTTATGTGTTTCCTCAAAGGCCTTCTTGAAGAAGTTACTGACCGC
 L  D  H  E  Y  T  T  K  E  V  F  R  K  N  F  F  N  D  W  R
360                      380                      400

AAAGGAAATGGCGGTGGAAGAGAGGGAAGTCATCAAGAGCCTGGACAAGTGTGACTTCAC
---+---------+---------+---------+---------+---------+---------
TTTCCTTTACCGCCACCTTCTCTCCCTTCAGTAGTTCTCGGACCTGTTCACACTGAAGTG
 K  E  M  A  V  E  E  R  E  V  I  K  S  L  D  K  C  D  F  T
420                      440                      460
```

FIG. 1C

```
GGAGATCCACAGATACTTTGTGGACAAGGCCGCAGCCCGGAAAGTCCTGAGCAGGGAGGA
------+---------+---------+---------+---------+---------+
CCTCTAGGTGTCTATGAAACACCTGTTCCGCGTCGGGCCTTTCAGGACTCGTCCCTCCT
 E  I  H  R  Y  F  V  D  K  A  A  A  R  K  V  L  S  R  E  E
        480                      500                     520

GAAGCAGAAGCTAAAAGAGAGGCAGAAAACTTCAGCAAGAGTTCGGCTACTGTATTTT
------+---------+---------+---------+---------+---------+
CTTCGTCTTCGATTTTCTCTCCGTCTTTTGAAGTCGTTCTCAAGCCGATGACATAAAA
 K  Q  K  L  K  E  E  A  E  K  L  Q  Q  E  F  G  Y  C  I  L
        540                      560                     580

AGATGGTCACCAAGAAAAAAATAGGCAACTTCAAGATTGAGCCGCCTGGCTTGTTCCGTGG
------+---------+---------+---------+---------+---------+
TCTACCAGTGGTTCTTTTTTTATCCGTTGAAGTTCTAACTCGGGGACCGAACAAGGCACC
 D  G  H  Q  E  K  I  G  N  F  K  I  E  P  P  G  L  F  R  G
        600                      620                     640

CCGTGGGGACCATCCCAAGATGGGGATGCTGAAGAGAAGGATCACGCCAGAGGATGTGGT
------+---------+---------+---------+---------+---------+
GGCACCCGGCTGGTAGGGTTCTACCCCTACGACTTCTCTTCCTAGTGCGGTCTCCTACACCA
 R  G  D  H  P  K  M  G  M  L  K  R  R  I  T  P  E  D  V  V
        660                      680                     700
```

FIG. 1D

```
TATCAACTGCAGCAGGAGACTCGAAGATCCCCGAGCCGGGCACCAGTGGAAGGA
----+----|----+----|----+----|----+----|----+----|----+----|
ATAGTTGACGTCGTCCTCCTGAGCTTCTAGGGGCTCGGCCCGTGGTCACCTTCCT
          I  N  C  S  R  D  S  K  I  P  E  P  P  A  G  H  Q  W  K  E
                                 720                              740                              760

GGTGCGCTCCGATAACACCGTGTCACGTGGCAGCTTGGACCGAGAGCCGTTCAGAACTC
----+----|----+----|----+----|----+----|----+----|----+----|
CCACGCGAGGCTATTGTGGCACAGTGCACCGTCGAACCTGGCTCTCGCAAGTCTTGAG
 V  R  S  D  N  T  V  T  W  L  A  A  W  T  E  S  V  Q  N  S
                    780                              800                              820

CATCAAGTACATCATGCTGAACCCTTGCTCGAAGCTGAAGGGGAGACAGCTTGGCAGAA
----+----|----+----|----+----|----+----|----+----|----+----|
GTAGTTCATGTAGTACGACTTGGGAACGAGCTTCGACTTCCCCCTCTGTCGAACCGTCTT
  I  K  Y  I  M  L  N  P  C  S  K  L  K  G  E  T  A  W  Q  K
                    840                              860                              880

GTTTGAAACAGCTCGAGCGCTGCGGGATTTGTGGACGAGATCCGCTCCCAGTACCGGGC
----+----|----+----|----+----|----+----|----+----|----+----|
CAAACTTTGTCGAGCTCGCGACGCCCCTAAACACCTGCTCTAGGCGAGGGTCATGGCCCG
 F  E  T  A  R  R  L  R  G  F  V  D  E  I  R  S  Q  Y  R  A
                    900                              920                              940
```

FIG. 1E

```
TGACTGGAAGTCTCGGGAAATGAAGACGAGACAGCGGGGTGGCCCTGTATTCATCGA
---+---------+---------+---------+---------+---------+--
ACTGACCTTCAGAGCCCTTACTTCTGCTCTGTCGCCACCGGACATAAAGTAGCT
                                            1000
 D  W  K  S  R  E  M  K  T  R  Q  R  A  V  A  L  Y  F  I  D
 960                  980

TAAGCTGGCACTGAGAGCAGGAAATGAGAAGGAGGACGGTGAGGGCCGACACCGTGGG
---+---------+---------+---------+---------+---------+--
ATTCGACCGTGACTCTCGTCCTTTACTCTTCCTGCCACTCCCGGCTGTGGCACCC
 K  L  A  L  R  A  G  N  E  K  E  D  G  E  A  A  D  T  V  G
 1020                              1060

CTGCTGTGTTCCCTCCGGGTGGAGCACGTCCAGCTGCACCCGGAGGCCGATGGTTGCCAACA
---+---------+---------+---------+---------+---------+--
GACGACAAGGAGGCGCACCTCGTGCAGGTCGACGTGGGCCTCCGGCTACCAACGGTTGT
 C  C  S  L  R  V  E  H  V  Q  L  H  P  E  A  D  G  C  Q  H
 1080                              1120

CGTGGTGGAATTTGACTTCCTGGGAAGGACTGCATCCGCTACTACAACAGAGTGCCGGT
---+---------+---------+---------+---------+---------+--
GCACCACCTTAAACTGAAGGACCCCTTCCTGACGTAGGCGATGATGTTGTCTCACGGCCA
 V  V  E  F  D  F  L  G  K  D  C  I  R  Y  Y  N  R  V  P  V
 1140                              1180
```

FIG. 1F

```
GGAGAAGCCGGTGTACAAGAACTTACAGCTCTTTATGGAGAACAAGGACCCCCGGGACGA
-----+---------+---------+---------+---------+---------+
CCTCTTCGGCCACATGTTCTTGAATGTCGAGAAATACCTCTTGTTCCTGGGGCCCTGCT
 E  K  P  V  Y  K  N  L  Q  L  F  M  E  N  K  D  P  R  D  D
              1200                 1220                 1240

CCTCTTCGACAGGCTGACCACGACCAGCCTGAACAAGCACCTCCAGGAGCTGATGGACGG
-----+---------+---------+---------+---------+---------+
GGAGAAGCTGTCCGACTGGTGCTGGTCGGACTTGTTCGTGGAGGTCCTCGACTACCTGCC
 L  F  D  R  L  T  T  T  S  L  N  K  H  L  Q  E  L  M  D  G
              1260                 1280                 1300

GCTGACGGCCAAGGTGTTCCGGACCTACAACGCCCTCCATCACTCTGCAGGAGCAGCTGCG
-----+---------+---------+---------+---------+---------+
CGACTGCCGGTTCCACAAGGCCTGGATGTTGCGGGAGTAGTGAGACGTCCTCGTCGACGC
 L  T  A  K  V  F  R  T  Y  N  A  S  I  T  L  Q  E  Q  L  R
              1320                 1340                 1360

GGCCCTGACGCGCGCCGAGGACAGCATAGCAGCTAAGATCTTATCCTACAACCGAGCCAA
-----+---------+---------+---------+---------+---------+
CCGGGACTGCGCGCGGCTCCTGTCGTATCGTCGATTCTAGAATAGGATGTTGGCTCGGTT
 A  L  T  R  A  E  D  S  I  A  A  K  I  L  S  Y  N  R  A  N
              1380                 1400                 1420
```

FIG. 1G

```
CCGAGTCGTGGCCATTCTCTGCAACCATCAGGAGCAACCCCCAGTACGTTCGAGAAGTC
-----+---------+---------+---------+---------+---------+
GGCTCAGCACCGGTAAGAGACGTTGGTAGTCGCTCGTTGGGGGTCATGCAAGCTCTTCAG
 R  V  V  A  I  L  C  N  H  Q  R  A  T  P  S  T  F  E  K  S
1440                         1460                        1480

GATGCAGAATCTCCAGACGAAGATCCAGGCAAAGAAGGAGCAAAGAAGGAGCAGGGGCTGAGGCCAGGGC
-----+---------+---------+---------+---------+---------+
CTACGTCTTAGAGGTCTGCTTCTAGGTCCGTTTCTTCCTCGTCCACCGACTCCGGTCCCG
 M  Q  N  L  Q  T  K  I  Q  A  K  K  E  Q  V  A  E  A  R  A
1500                         1520                        1540

AGAGCTGAGGAGGGCGAGGCTGAGCACAAAGCCCAAGGGGATGGCAAGTCCAGGAGTGT
-----+---------+---------+---------+---------+---------+
TCTCGACTCCTCCCGCTCCGACTCGTGTTTCGGGTTCCCCTACCGTTCAGTCCTCCTCACA
 E  L  R  R  A  R  A  E  H  K  A  Q  G  D  G  K  S  R  S  V
1560                         1580                        1600

CCTGGAGAAGAAGAGGCGGCTCCTGGAGAAGCTGCAGGAGCAGCTGGCCAGCTGAGTGT
-----+---------+---------+---------+---------+---------+
GGACCTCTTCTTCTCCGCCGAGGACCTCTTCGACGTCCTCGTCGACCGGTCGACTCACA
 L  E  K  K  R  R  L  L  E  K  L  Q  E  Q  L  A  Q  L  S  V
1620                         1640                        1660
```

FIG. 1H

```
GCAGGCCACGGACAAGGAGGAGAACAAGCAGGTGGGCCCTGGGCACGTTCCAAGCTCAACTA
----+----|----+----|----+----|----+----|----+----|----+----|
CGTCCGGTGCCTGTTCCTCCTCTTGTTCGTCCACCGGGACCCGTGCAAGGTTCGAGTTGAT
            1680            1700            1720
  Q  A  T  D  K  E  E  N  K  Q  V  A  L  G  T  S  K  L  N  Y

CCTGACCCCAGGATCAGCATTGCCTGGTGCAAGCGGTTCAGGGTGCCAGTGGAGAAGAT
----+----|----+----|----+----|----+----|----+----|----+----|
GGACCTGGGGTCCTAGTCGTAACGGACCACGTTCGCCAAGTCCCACGGTCACCTCTTCTA
            1740            1760            1780
  L  D  P  R  I  S  I  A  W  C  K  R  F  R  V  P  V  E  K  I

CTACAGCAAAACACAGCGGGAGAGGTTCGCCTgGGCTCTCGCCATGGCAGGAGAAGACTT
----+----|----+----|----+----|----+----|----+----|----+----|
GATGTCGTTTTGTGTCGCCCTCTCCAAGCGGACCCGAGAGCCGGTACCGTCCTCTTCTGAA
            1800            1820            1840
  Y  S  K  T  Q  R  E  R  F  A  W  A  L  A  M  A  G  E  D  F

TGAATTCTAACGACGAGCCGTGTGAAACTTCTTTTGTATGTGTGTGTTTTTTCACT
----+----|----+----|----+----|----+----|----+----|----+----|
ACTTAAGATTGCTGCTCGGCACAACTTTGAAGAAAACATACACACAAAAAAGTGA
  E  F  *         1860            1880            1900
ATTAAAGCAGTACTGGGAATTTGTACAATAAAAAAAAAAAAAAAAAAAAAAA
----+----|----+----|----+----|----+----|----+----|----+----|
TAATTCGTCATGACCCCTTAAACATGTTATTTTTTTTTTTTTTTTTTTTTTT
```

FIG. 2A

```
TopIα    3 VVRLLRLRAALTL..........................LGEVPRRPAS  25
           .  ||.|:|   .:                              |.  :...:
TopI   133 IKPLKRPRDEDDVDYKPKKIKTEDTKKEKKRKLEEEEDGKLKKPKNKDKD 182

26 RGVPGSRRTQKGSG........ARWEKEHEDGVKWRQLEHKGPYFAPPYE  68
           :||:.||       ...:|    .::.|:.|::||:.:|: ||||| |||
       183 KKVPEPDNKKKKKPKKEEEQKWKWWEEERYPEGIKWKFLEHKGPVFAPPYE 232

69 PLPDGVRFFYEGRPVRLSVPAEEVPTFYGRMLDHEYTTKEVFRKNFFNDW  118
           |||:||:||||:|   :||: ::||||  |||||||||||:||||||:||
       233 PLPENVKFYYDGKVMKLSPKAEEVATFFAKMLDHEYTTKEIFRKNFFKDW 282

119 RKEMAVEEREVIKSLDKCDFTEIHRYFVDKAAARKVLSREEKQKLKEEAE  168
           ||||  ||::|| :. |||| |:.  |||::.||::|:||:||:|:|:.|
       283 RKEMTNEEKNIITNLSKCDFTQMSQYFKAQTEARKQMSKEEKLKIKEENE 332

169 KLQQEFGYCILDGHQEKIGNFKIEPPGLFRGRGDHPKMGMLKRRITPEDV 218
           ||: :||:|||| :||| ||||||||||||||:||||||||||||||:|:
       333 KLLKEYGFCIMDNHKERIANFKIEPPGLFRGRGNHPKMGMLKRRIMPEDI 382

219 VINCSRDSKIPEPPAGHQWKEVRSDNTVTWLAAWTESVQNSIKYIMLNPC 268
           :||||:|:||| ||| |.||||| ||||:||||:|.:||||||||||||:
       383 IINCSKDAKVPSPPPGHKWKEVRHDNKVTWLVSWTENIQGSIKYIMLNPS 432
```

FIG. 2B

```
269 SKLKGETAWQKFETARRLRGFVDEIRSQYRADWKSREMKTRQRAVALYFI 318
    |::.||.|||..|||..|||.|| ||.||.|||.|:.|||||||||||
433 SRIKGEKDWQKYETARRLKKCVDKIRNQYREDWKSKEMKVRQRAVALYFI 482

319 DKLALRAGNEKEDGEAADTVGCCSLRVEHVQLHPEADGCQHVVEFDFLGK 368
    |||||||||||:|||:|||||||||||||:..|||.||: :.||||||
483 DKLALRAGNEKEEGETADTVGCCSLRVEHINLHPELDGQEYVVEFDFLGK 532

369 DCIRYNNRVPVEKPVYKNLQLFMENKDPRDDLFDRLTTTSLNKHLQELMD 418
    |:||||:|||||:|.||||||||||:|.:||||||| |.:|||||||:|:|
533 DSIRYYNKVPVEKRVFKNLQLFMENKQPEDDLFDRLNTGILNKHLQDLME 582

419 GLTAKVFRTYNASITLQEQLRALTRAEDSIAAKILSYNRANRVVAILCNH 468
    ||||||||||||||||:::.|:.||: ::.|||.|||||||||.||||||
583 GLTAKVFRTYNASITLQQQLKELTAPDENIPAKILSYNRANRAVAILCNH 632

469 QRATPSTFEKSMQNLQTKIQAKKEQVAEARAELRRARAEHKAQGDGKSRS 518
    |||.|.||||||:||||||.||:|||::||:||:|| :|: |:::.:
633 QRAPPKTFEKSMMNLQTKIDAKKEQLADARRDLKSAKADAKVMKDAKTKK 682

519 VLEKKRRLLEKLQEQLAQLSVQATDKEENKQVALGTSKLNYLDPRISIAW 568
    |::|::. :::|||.|:|||:|::|||||||||:|||||||||||||:|:||
683 VVESKKKAVQRLEEQLMKLEVQATDREENKQIALGTSKLNYLDPRITVAW 732
```

FIG. 2C

```
569  CKRFRVPVEKIYSKTQRERFAWALAMAGEDFEF  601
     ||::  ||:||||.||||:..||:||:||
733  CKKWGVPIEKIYNKTQREKFAWAIDMADEDYEF  765
```

HUMAN DNA TOPOISOMERASE I α

This application is a continuation-in-part of PCT/US94/05701, filed May 18, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human DNA topoisomerase I alpha (hTopI-α). The invention also relates to inhibiting the action of such polypeptides.

DNA topoisomerase I and II catalyze the breaking and rejoining of DNA strands in a way that allows the strands to pass through one another, thus altering the topology of DNA. Type I topoisomerase recognizes double-stranded DNA but only breaks on strand in the process of relaxing DNA, while the type II enzyme breaks both strands of duplex DNA. Both enzymes can perform a variety of similar topological inter-conversions, including relaxation of super coiled DNA, knotting and unknotting and catenation and decatenation of duplex DNA. Topoisomerase I is ATP-independent, while Topoisomerase II requires energy.

Both topoisomerase I and II can provide the topological inter-conversions necessary for transcription and replication. For example, topoisomerase I can provide the necessary unlinking activity for efficient in vitro DNA replication (Minden, et al., J. Biol. Chem., 260:9316, (1985)), however, topoisomerase II can also facilitate the replication of SV40 DNA by HeLa cell lysates (Yang, et al., Proceedings of the National Academy of Sciences, U.S.A., 84:950, (1987)). Genetic studies in yeast reveal that both replication and transcription proceed in single mutants deficient in either topoisomerase I or II (Goto, et al., Proceedings of the National Academy of Sciences, U.S.A., 82:7178 (1985)). In cells lacking both topoisomerases, transcription and replication are dramatically reduced (Uemura, et al., EMBO Journal, 5:1003 (1986)).

Several lines of evidence suggest that topoisomerase I normally functions during transcription. The enzyme has been shown to be localized preferentially to actively transcribed loci by immunofluorescence (Fleishmann, et al., Proceedings of the National Academy of Sciences, U.S.A., 81:6958 (1984)), andby co-immunoprecipitation with transcribed DNA (Gilmore, et al., Cell, 44:401, (1986)). Furthermore, topoisomerase I cleavage sites have been mapped to regions in and around transcribed DNA (Bonner, et al., Cell, 41:541 (1985)). Nonetheless, at least in yeast, topoisomerase II can apparently substitute for the functions of topoisomerase I in transcription.

While all cells utilize Topoisomerase I and II for transcription and replication, cells with a high amount of transcription and replication, eg. cancerous cells, have a much higher concentration of Topoisomerase I and II.

Topoisomerase I has been used to classify autoimmune disease. Autoimmune diseases are diseases in which an animal's immune system attacks its own tissues. Often the various types of autoimmune disease can be characterized based upon the specificity of autoantibodies which are produced. For example, it is well known that the serum of patients having the connective tissue autoimmune disease progressive systemic sclerosis, also known as scleroderma, frequently contain antibodies to such nuclear antigens as topoisomerase I. Thus, the ability to accurately detect the presence of antibodies reactive with topoisomerase I can greatly assist in evaluating the prognosis and planning, or monitoring, of the appropriate therapy for patients with scleroderma.

A 3645-base pair human topoisomerase I cDNA clone and a mutated version of the cDNA encoding a protein with phenylalanine instead of tyrosine at position 723 have been overexpressed two to five fold in stably transfected baby hamster kidney cells. The results of this overexpression indicate that tyrosine 723 is essential for enzyme activity and is consistent with predictions based on homology comparisons with the yeast enzymes, that this is the active-site tyrosine in the human topoisomerase I. (Madden, K. R. and Champoux, J. J., Cancer Research, 52:525–532, (1992)).

Also, cDNA clones encoding human topoisomerase I have been isolated from an expression vector library screened with autoimmune anti-topoisomerase I serum. The sequence data shows that the catalytically active 67.7-kDa fragment is comprised of the carboxyl terminus. (D'Arpa, P. et al., Proc. Natl. Acad. Sci. U.S.A., 85:2543–2547, (1988)).

cDNA molecules coding for eukaryotic topoisomerase I polypeptide which encode at least one epitope for autoantibodies to eukaryotic topoisomerase I and cloning vehicles capable of expressing these cDNA molecules are disclosed in U.S. Pat. No. 5,070,192.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, to treat and/or prevent neoplasia, for example, tumors and adenocarcinoma of the colon, and retroviral infections.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

3

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1H, collectively show the cDNA sequence (SEQ ID NO:1) and corresponding deduced amino acid sequence (SEQ ID NO:2) of hTopI-α. The polypeptide encoded by the amino acid sequence shown is the mature form of the polypeptide. The standard one letter abbreviation for amino acids is used. Sequencing was performed using a 373 automated DNA sequencer (Applied Biosystems, Inc.).

FIGS. 2A–2C, collectively, show a comparison of hTOPI-α (SEQ ID NO:2) and human topoisomerase I (SEQ ID NO:5) at the amino acid level. The upper line is hTOPI-α.

In accordance with an aspect of the present invention, there is provided an isolated nucleic acid (polynucleotide) which encodes for the mature polypeptide having the deduced amino acid sequence of FIGS. 1A–1H (collectively, SEQ ID NO:2) or for the mature polypeptide encoded by the cDNA of the clone deposited as ATCC Deposit No. 75714 on Mar. 18, 1994.

The ATCC number referred to above is directed to a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

A polynucleotide encoding a polypeptide of the present invention was obtained from a fetal brain cDNA library. It is homologous to human topoisomerase I. It contains an open reading frame encoding a protein of 601 amino acid residues and it is structurally related to human DNA topoisomerase I showing 86% similarity and 70% identity at the amino acid level. Further, hTopI-α shows 83% similarity and 67% identity to human topoisomerase I as published by D'Arpa et al.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1H (collectively, SEQ ID NO:1) or that of the deposited clone or may be a different coding sequence which coding sequence, as a result of the redundancy or degeneracy of the genetic code, encodes the same mature polypeptide as the DNA of FIGS. 1A–1H (collectively, SEQ ID NO:1) or the deposited cDNA.

The polynucleotide which encodes for the mature polypeptide of FIGS. 1A–1H (collectively, SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1H (collectively, SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1H (collectively, SEQ ID NO:2) or the same mature polypeptide encoded by the cDNA of the deposited clone as well as variants of such polynucleotides which variants encode for a fragment, derivative or analog of the polypeptide of FIGS. 1A–1H (collectively, SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1H (collectively, SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length hTopI-α gene may be used as a hybridization probe for a cDNA library to isolate the full length CysE gene and to isolate other genes which have a high sequence similarity to the hTopI-α gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1H (collectively, SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIGS. 1A–1H (collectively, SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1H (collectively, SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1H (collectively, SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably a 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli$.

The vector containing the appropriate DNA sequence as hereinabove described, as well as an appropriate promoter or control sequence, may be employed to transforman appropriate host to permit the host to express the protein.

As representative examples of appropriate hosts, there may be mentioned: bacterial cells, such as $E.\ coli$, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected bycalcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.\ coli$ and $S.\ cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The present invention is also directed to an assay to identify compounds which inhibit hTopI-α. DNA, hTopI-α and a potential compound are combined under appropriate conditions for a length of time sufficient for hTopI-α to act on the single strand DNA. The DNA is then analyzed, for example, by gel electrophoresis, to determine whether hTopI-α functioned properly and in this way it could be determined whether the compound effectively inhibits hTopI-α.

Potential antagonists include an antibody, or in some cases, an oligopeptide, which bind to the polypeptide. Alternatively, a potential antagonist may be a closely related polypeptide which is a mutant or inactive form of the polypeptide such that substrate is occupied and the action of hTopI-α is prevented. Since the polypeptide of the present invention acts intra-cellularly the antibodies may be produced intra-cellularly as a single chain antibody by procedures known in the art, such as transforming the appropriate cells with DNA encoding the single chain antibody to prevent the function of hTopI-α.

Another antagonist compound is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of hTopI-α. The antisense RNA oligonucleotide hybridizes to the mRNA in vivo and blocks translation of the mRNA molecule into hTopI-α polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptide of the present invention.

Another potential antagonist compound includes a small molecule which is capable of passing through the cell membrane and which binds to and occupies the catalytic site of the polypeptide thereby making the catalytic site inaccessible to substrate such that normal biological activity is prevented. Examples of small molecules include but are not limited to small peptides or peptide-like molecules.

The antagonist compounds may be employed to treat tumors since specific inhibition of htopI-α will inhibit tumor cell growth by blocking tumor cell DNA replication. The antagonists may also be used to treat retroviral infections by inhibiting hTopI-α and therefore blocking initiation and replication of the virus. The antagonists may also be used to treat adenocarcinoma of the colon, since metastases are prevented by blocking DNA transcription of the cancerous cells.

The antagonist compounds may be employed in a composition with a pharmaceutically acceptable carrier, e.g., as hereinafter described.

The antagonist compounds of the present invention may be employed in combination with a suitable pharmaceutical carrier. Such compositions comprise a therapeutically effective amount of the compound and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, arian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of hTopI-α will allow a diagnosis of a disease or a susceptibility to a disease, for example, related to improper transcription and replication.

Individuals carrying mutations in the human gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hTopI-α can be used to identify and analyze mutations. For example, deletions and insertions can be detected by a change in size of the amplified product in comparison to the normal genotype. Point mutations can be identified by hybridizing amplified DNA to radiolabeled hTopI-α RNA or alternatively, radiolabeled hTopI-α antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of hTopI-α protein in various tissues since an over-expression of the proteins compared to normal control tissue samples can detect the presence of abnormal cellular proliferation, i.e., cancer. A high level of this protein is indicative of cancer since some human colon carcinoma cells have increased levels of hTopI-α. They may also be indicative of autoimmune diseases, such as scleroderma, rheumatoid arthritis and AIDS related complex. Assays used to detect levels of hTopI-α protein in a sample derived from a host are well-known to those of skill in the art and include radioimmunoassays, competitive-binding assays, Western Blot analysis and preferably an ELISA assay. An ELISA assay initially comprises preparing an antibody specific to the hTopI-α antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any hTopI-α proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to hTopI-α. Unattached reporter antibody is then washed out. Peroxidase substrates are then added to the dish and the amount of color developed in a given time period is a measurement of the amount of hTopI-α protein present in a given volume of patient sample when compared against a standard curve.

A competition assay may be employed wherein antibodies specific to hTopI-α are attached to a solid support and labeled hTopI-α and a sample derived from the host are passed over the solid support and the amount of label detected attached to the solid support can be correlated to a quantity of hTopI-α in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milsrein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention. The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Expression of Recombinant hTopI-α in COS Cells

The expression of plasmid, pcDNAtopI HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire hTopI-αprecursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Cormoily, and R. Lerner, 1984, Cell 37, 767). The infusion of HA tag to our target protein allows easy detection of the recombinant protein with an antibody that recognizes the HA epitope.

The plasmid construction strategy is described as follows:

The expression plasmid pcDNATopI-α ATCC #75714, encoding for hTopI-α was constructed by PCR on the pBLTopI-α using two primers: the 5' primer 5' CGGGATC-CATGCGCGTGGTGCGG 3' (SEQ ID NO:3) contains a BamHI site followed by 15 nucleotides of HhTopI-α coding sequence starting from the initiation codon; the 3' sequence 5' CGCTCTAGATCAAGCGTAGTCT GGGACGTCG-TATGGGTAGAATTCAAAGTCTTCTCC 3' (SEQ ID NO:4) contains complementary sequences to an Xba I site, translation stop codon, HA tag and the last 18 nucleotides of the hTopI-α coding sequence (not including the stop codon). Therefore, the PCR product contains a Bam HI site, active hTopI-α coding sequence followed by HA tag fused in frame, a translation termination stop codon next to the HA tag, and an Xba I site. The PCR amplified DNA fragment and the vector, pcDNAI/Amp, were digested with Bam HI and Xba I restriction enzyme and ligated. The ligation mixture was transformed into E. coli strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant hTopI-α, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the hTopI-α HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 2

In vitro Transcription and Translation of hTopI-α

The in vitro transcription and translation of the hTopI-α was carried out using the TNT Coupled Reticulocyte Lysate System (Promega, Madison, Wis.). The plasmid vector used is pBLSK. The cDNA encoding for hTopI-α was cloned directionally EcoRI to XhoI with the EcoRI site defining the 5' end of the gene and the XhoI site defining the 3' end of the gene. The gene was inserted in the T3 direction. T3 defines a bacteriophage RNA polymerase which recognizes a specific promoter, and transcribes the DNA into a mRNA. One microgram of the pBLSKhTOPIα was incubated with 25 μl of TNT rabbit reticulocyte lysate, 2 μl TNT reaction buffer, 1 μl T3 RNA polymerase, 1 μl of amino acid mixture minus methionine (1 mM), 4 μl of $^{35}$S-methionine (1,000 Ci/mmol) at 10 mCi/ml, 1 μl RNasin ribonuclease inhibitor (40 U/μl) in 50 μl of final volume at 37° C. for 1.5 hour. 5 μl of the reaction mixture was mixed with loading buffer, boiled for 5 minutes and loaded on a 10% SDS polyacrylamide gel to separate the protein. The gel was then fixed 10% acetic acid, 10% methanol at room temperature for 30 minutes, soaked in Amplify solution (Amersham) at room temperature for 1.5 hours, dried, and subjected to autoradiograph. The observed molecular weight of the hTopI-α in this system is 70 kD, which agrees with the predicted molecular weight by the sequence.

EXAMPLE 3

Expression Pattern of hTopI-α in Human Tissue

Northern blot analysis was carried out to examine the levels of expression of hTopIα in human tissues. Total cellular RNA samples were isolated with RNAzol™ B system (Biotecx Laboratories, Inc. Houston, Tex. 77033). About 10 μg of total RNA isolated from each human tissue specified was separated on 1% agarose gel and blotted onto a nylon filter. (Sambrook, Fritsch, and Manjarls, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime—3 Prime, Inc. 5603 Arapahoe Road, Boulder, Colo. 80303). The filter was then hybridized with radioactive labeled full length hTopI-α gene at 1,000,000 cpm/ml in 0.5M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for hTopIα is present in all the tissues with abundance in ovary, testes, lung, spleen and prostate.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least a 95% identity to a member selected from the group consisting of:
   (a) a polynucleotide encoding a polypeptide comprising amino acids 2 to 601 of SEQ ID NO:2; and
   (b) the complement of (a).

2. The isolated polynucleotide of claim 1 wherein said member is (a).

3. The isolated polynucleotide of claim 1 wherein said member is (a) and the polypeptide comprises amino acids 1 to 601 of SEQ ID No:2.

4. The isolated polynucleotide of claim 1 comprising a polynucleotide encoding a polypeptide comprising the amino acid sequence identical to amino acids 2 to 601 of SEQ ID NO:2.

5. The isolated polynucleotide of claim 1, wherein the polynucleotide is DNA.

6. The isolated polynucleotide of claim 1 comprising a polynucleotide encoding a polypeptide comprising the amino sequence identical to amino acids 1 to 601 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide.

12. A process for producing a polypeptide comprising:
expressing from a recombinant cell containing the polynucleotide of claim 4 the polypeptide encoded by said polynucleotide.

13. A process for producing a polypeptide comprising:
expressing from a recombinant cell containing the polynucleotide of claim 6 the polypeptide encoded by said polynucleotide.

14. The isolated polynucleotide of claim 1 comprising nucleotides 8 to 1862 of SEQ ID NO:1.

15. The isolated polynucleotide of claim 1 comprising nucleotides 5 to 1865 of SEQ ID NO:1.

16. The isolated polynucleotide of claim 1 comprising the nucleotides of the sequence of SEQ ID NO:1.

17. An isolated polynucleotide comprising a polynucleotide having at least a 95% identity to a member selected from the group consisting of:
(a) a polynucleotide encoding the same mature polypeptide encoded by the human cDNA in ATCC Deposit No. 75714; and
(b) the complement of (a).

18. The isolated polynucleotide of claim 17, wherein the member is (a).

19. The isolated polynucleotide of claim 17, wherein said polynucleotide comprises DNA identical to the coding portion of the human cDNA in ATCC Deposit No. 75714 which encodes a mature polypeptide.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1917 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
GCAGATGCGC  GTGGTGCGGC  TGCTGCGGCT  CCGGGCGGCT  CTGACGCTGC  TCGGGGAGGT    60
CCCCCGCCGC  CCGGCCTCCC  GGGGTGTCCC  GGGCTCGCGC  AGGACGCAGA  AGGGCAGTGG   120
AGCCAGGTGG  GAGAAGGAGA  AGCACGAAGA  CGGGGTGAAG  TGGAGACAGC  TGGAGCACAA   180
GGGCCCGTAC  TTCGCACCCC  CATACHAGCC  CCTTCCCGAC  GGAGTGCGTT  TCTTCTATGA   240
AGGAAGGCCT  GTGAGATTGA  GCGTGCCAGC  GGAGGAGGTC  CCCACTTTTT  ATGGGAGGAT   300
GTTAGATCAT  GAATACACAA  CAAAGGAGGT  TTTCCGGAAG  AACTTCTTCA  ATGACTGGCG   360
AAAGGAAATG  GCGGTGGAAG  AGAGGGAAGT  CATCAAGAGC  CTGGACAAGT  GTGACTTCAC   420
GGAGATCCAC  AGATACTTTG  TGGACAAGGC  CGCAGCCCGG  AAAGTCCTGA  GCAGGGAGGA   480
GAAGCAGAAG  CTAAAAGAAG  AGGCAGAAAA  ACTTCAGCAA  GAGTTCGGCT  ACTGTATTTT   540
AGATGGTCAC  CAAGAAAAAA  TAGGCAACTT  CAAGATTGAG  CCGCCTGGCT  TGTTCCGTGG   600
CCGTGGCGAC  CATCCCAAGA  TGGGATGCT   GAAGAGAAGG  ATCACGCCAG  AGGATGTGGT   660
TATCAACTGC  AGCAGGGACT  CGAAGATCCC  CGAGCCGCCG  GCGgGGCACC  AGTGGAAGGA   720
GGTGCGCTCC  GATAACACCG  TCACGTGGCT  GGACAGCTTG  ACCGAGAGCG  TTCAGAACTC   780
CATCAAGTAC  ATCATGCTGA  ACCCTTGCTC  GAAGCTGAAG  GGGAGACAG   CTTGGCAGAA   840
GTTTGAAACA  GCTCGACGCC  TGCGGGGATT  TGTGGACGAG  ATCCGCTCCC  AGTACCGGGC   900
TGACTGGAAG  TCTCGGGAAA  TGAAGACGAG  ACAGCGGGCG  GTGGCCCTGT  ATTTCATCGA   960
TAAGCTGGCA  CTGAGAGCAG  GAAATGAGAA  GGAGGACGGT  GAGGCGGCCG  ACACCGTGGG  1020
CTGCTGTTCC  CTCCGCGTGG  AGCACGTCCA  GCTGCACCCG  GAGGCCGATG  GTTGCCAACA  1080
CGTGGTGGAA  TTTGACTTCC  TGGGGAAGGA  CTGCATCCGC  TACTACAACA  GAGTGCCGGT  1140
GGAGAAGCCG  GTGTACAAGA  ACTTACAGCT  CTTTATGGAG  AACAAGGACC  CCGGGACGA   1200
CCTCTTCGAC  AGGCTGACCA  CGACCAGCCT  GAACAAGCAC  CTCCAGGAGC  TGATGGACGG  1260
GCTGSCGGCC  AAGGTGTTCC  GGACCTACAA  CGCCTCCATC  ACTCTGCAGG  AGCAGCTGCG  1320
GGCCCTGACG  CGCGCCGAGG  ACAGCATAGC  AGCTAAGATC  TTATCCTACA  ACCGAGCCAA  1380
CCGAGTCGTG  GCCATTCTCT  GCAACCATCA  GCGAGCAACC  CCCAGTACGT  TCGAGAAGTC  1440
GATGCAGAAT  CTCCAGACGA  AGATCCAGGC  AAAGAAGGAG  CAGGTGGCTG  AGGCCAGGGC  1500
AGAGCTGAGG  AGGGCGAGGG  CTGAGCACAA  AGCCCAAGGG  GATGGCAAGT  CCAGGAGTGT  1560
CCTGGAGAAG  AAGAGGCGGC  TCCTGGAGAA  GCTGCAGGAG  CAGCTGGCGC  AGCTGAGTGT  1620
GCAGGCCACG  GACAAGGAGG  AGAACAAGCA  GGTGGCCCTG  GCACGTCCA   AGCTCAACTA  1680
CCTGGACCCC  AGGATCAGCA  TTGCCTGGTG  CAAGCGGTTC  AGGGTGCCAG  TGGAGAAGAT  1740
CTACAGCAAA  ACACAGCGGG  AGAGGTTCGC  CTGGGCTCTC  GCCATGGCAG  GAGAAGACTT  1800
```

```
TGAATTCTAA CGACGAGCCG TGTTGAAACT TCTTTTGTAT GTGTGTGTGT TTTTTTCACT  1860

ATTAAAGCAG TACTGGGGAA TTTTGTACAA TAAAAAAAAA AAAAAAAAA  AAAAAA      1917
```

( 2 ) INFORMATION FOR SEQ ID NO:2:

( i ) SEQUENCE CHARACTERISTICS:
        ( A ) LENGTH: 601 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met Arg Val Val Arg Leu Leu Arg Leu Arg Ala Ala Leu Thr Leu
                  5                  10                 15

Leu Gly Glu Val Pro Arg Arg Pro Ala Ser Arg Gly Val Pro Gly
                 20                  25                 30

Ser Arg Arg Thr Gln Lys Gly Ser Gly Ala Arg Trp Glu Lys Glu
                 35                  40                 45

Lys His Glu Asp Gly Val Lys Trp Arg Gln Leu Gly His Lys Gly
                 50                  55                 60

Pro Tyr Phe Ala Pro Pro Tyr Glu Pro Leu Pro Asp Gly Val Arg
                 65                  70                 75

Phe Phe Tyr Glu Gly Arg Pro Val Arg Leu Ser Val Pro Ala Glu
                 80                  85                 90

Glu Val Pro Thr Phe Tyr Gly Arg Met Leu Asp His Glu Tyr Thr
                 95                 100                105

Thr Lys Glu Val Phe Arg Lys Asn Phe Phe Asn Asp Trp Arg Lys
                110                 115                120

Glu Met Ala Val Glu Glu Arg Glu Val Ile Lys Ser Leu Asp Lys
                125                 130                135

Cys Asp Phe Thr Glu Ile His Arg Tyr Phe Val Asp Lys Ala Ala
                140                 145                150

Ala Arg Lys Val Leu Ser Arg Glu Glu Lys Gln Lys Leu Lys Glu
                155                 160                165

Glu Ala Glu Lys Leu Gln Gln Glu Phe Gly Tyr Cys Ile Leu Asp
                170                 175                180

Gly His Gln Glu Lys Ile Gly Asn Phe Lys Ile Glu Pro Pro Gly
                185                 190                195

Leu Phe Arg Gly Arg Gly Asp His Pro Lys Met Gly Met Leu Lys
                200                 205                210

Arg Arg Ile Thr Pro Glu Asp Val Val Ile Asn Cys Ser Arg Asp
                215                 220                225

Ser Lys Ile Pro Glu Pro Pro Ala Gly His Gln Trp Lys Glu Val
                230                 235                240

Arg Ser Asp Asn Thr Val Thr Trp Leu Ala Ala Trp Thr Glu Ser
                245                 250                255

Val Gln Asn Ser Ile Lys Tyr Ile Met Leu Asn Pro Cys Ser Lys
                260                 265                270

Leu Lys Gly Glu Thr Ala Trp Gln Lys Phe Glu Thr Ala Arg Arg
                275                 280                285

Leu Arg Gly Phe Val Asp Glu Ile Arg Ser Gln Tyr Arg Ala Asp
                290                 295                300

Trp Lys Ser Arg Glu Met Lys Thr Arg Gln Arg Ala Val Ala Leu
                305                 310                315
```

-continued

| | | | | | | | | | | | | | |
|---|---|---|---|---|---|---|---|---|---|---|---|---|---|
| Tyr | Phe | Ile | Asp | Lys 320 | Leu | Ala | Leu | Arg | Ala 325 | Gly | Asn | Glu | Lys | Glu 330 |
| Asp | Gly | Glu | Ala | Ala 335 | Asp | Thr | Val | Gly | Cys 340 | Cys | Ser | Leu | Arg | Val 345 |
| Glu | His | Val | Gln | Leu 350 | His | Pro | Glu | Ala | Asp 355 | Gly | Cys | Gln | His | Val 360 |
| Val | Glu | Phe | Asp | Phe 365 | Leu | Gly | Lys | Asp | Cys 370 | Ile | Arg | Tyr | Tyr | Asn 375 |
| Arg | Val | Pro | Val | Glu 380 | Lys | Pro | Val | Tyr | Lys 385 | Asn | Leu | Gln | Leu | Phe 390 |
| Met | Glu | Asn | Lys | Asp 395 | Pro | Arg | Asp | Asp | Leu 400 | Phe | Asp | Arg | Leu | Thr 405 |
| Thr | Thr | Ser | Leu | Asn 410 | Lys | His | Leu | Gln | Glu 415 | Leu | Met | Asp | Gly | Leu 420 |
| Thr | Ala | Lys | Val | Phe 425 | Arg | Thr | Tyr | Asn | Ala 430 | Ser | Ile | Thr | Leu | Gln 435 |
| Glu | Gln | Leu | Arg | Ala 440 | Leu | Thr | Arg | Ala | Glu 445 | Asp | Ser | Ile | Ala | Ala 450 |
| Lys | Ile | Leu | Ser | Tyr 455 | Asn | Arg | Ala | Asn | Arg 460 | Val | Val | Ala | Ile | Leu 465 |
| Cys | Asn | His | Gln | Arg 470 | Ala | Thr | Pro | Ser | Thr 475 | Phe | Glu | Lys | Ser | Met 480 |
| Gln | Asn | Leu | Gln | Thr 485 | Lys | Ile | Gln | Ala | Lys 490 | Lys | Glu | Gln | Val | Ala 495 |
| Glu | Ala | Arg | Ala | Glu 500 | Leu | Arg | Arg | Ala | Arg 505 | Ala | Glu | His | Lys | Ala 510 |
| Gln | Gly | Asp | Gly | Lys 515 | Ser | Arg | Ser | Val | Leu 520 | Glu | Lys | Lys | Arg | Arg 525 |
| Leu | Leu | Glu | Lys | Leu 530 | Gln | Glu | Gln | Leu | Ala 535 | Gln | Leu | Ser | Val | Gln 540 |
| Ala | Thr | Asp | Lys | Glu 545 | Glu | Asn | Lys | Gln | Val 550 | Ala | Leu | Gly | Thr | Ser 555 |
| Lys | Leu | Asn | Tyr | Leu 560 | Asp | Pro | Arg | Ile | Ser 565 | Ile | Ala | Trp | Cys | Lys 570 |
| Arg | Phe | Arg | Val | Pro 575 | Val | Glu | Lys | Ile | Tyr 580 | Ser | Lys | Thr | Gln | Arg 585 |
| Glu | Arg | Phe | Ala | Trp 590 | Ala | Leu | Ala | Met | Ala 595 | Gly | Glu | Asp | Phe | Glu 600 |
| Phe | | | | | | | | | | | | | | |

( 2 ) INFORMATION FOR SEQ ID NO:3:

( i ) SEQUENCE CHARACTERISTICS:
        ( A ) LENGTH: 23 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

CGGGATCCAT GCGCGTGGTG CGG                                       23

( 2 ) INFORMATION FOR SEQ ID NO:4:

( i ) SEQUENCE CHARACTERISTICS:
        ( A ) LENGTH: 57 BASE PAIRS
        ( B ) TYPE: NUCLEIC ACID ( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:4:

```
CGCTCTAGAT CAAGCGTAGT CTGGGACGTC GTATGGGTAG AATTCAAAGT CTTCTCC    57
```

( 2 ) INFORMATION FOR SEQ ID NO:5:

( i ) SEQUENCE CHARACTERISTICS:
( A ) LENGTH: 633 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:5:

```
Ile Lys Pro Leu Lys Arg Pro Arg Asp Glu Asp Val Asp Tyr
              5                  10                      15

Lys Pro Lys Lys Ile Lys Thr Glu Asp Thr Lys Lys Glu Lys Lys
              20                 25                      30

Arg Lys Leu Glu Glu Glu Glu Asp Gly Lys Leu Lys Lys Pro Lys
              35                 40                      45

Asn Lys Asp Lys Asp Lys Lys Val Pro Glu Pro Asp Asn Lys Lys
              50                 55                      60

Lys Lys Pro Lys Lys Glu Glu Glu Gln Lys Trp Lys Trp Trp Glu
              65                 70                      75

Glu Glu Arg Tyr Pro Glu Gly Ile Lys Trp Lys Phe Leu Glu His
              80                 85                      90

Lys Gly Pro Val Phe Ala Pro Pro Tyr Glu Pro Leu Pro Glu Asn
              95                 100                     105

Val Lys Phe Tyr Tyr Asp Gly Lys Val Met Lys Leu Ser Pro Lys
              110                115                     120

Ala Glu Glu Val Ala Thr Phe Phe Ala Lys Met Leu Asp His Glu
              125                130                     135

Tyr Thr Thr Lys Glu Ile Phe Arg Lys Asn Phe Phe Lys Asp Trp
              140                145                     150

Arg Lys Glu Met Thr Asn Glu Glu Lys Asn Ile Ile Thr Asn Leu
              155                160                     165

Ser Lys Cys Asp Phe Thr Gln Met Ser Gln Tyr Phe Lys Ala Gln
              170                175                     180

Thr Glu Ala Arg Lys Gln Met Ser Lys Glu Glu Lys Leu Lys Ile
              185                190                     195

Lys Glu Glu Asn Glu Lys Leu Leu Lys Glu Tyr Gly Phe Cys Ile
              200                205                     210

Met Asp Asn His Lys Glu Arg Ile Ala Asn Phe Lys Ile Glu Pro
              215                220                     225

Pro Gly Leu Phe Arg Gly Arg Gly Asn His Pro Lys Met Gly Met
              230                235                     240

Leu Lys Arg Arg Ile Met Pro Glu Asp Ile Ile Ile Asn Cys Ser
              245                250                     255

Lys Asp Ala Lys Val Pro Ser Pro Pro Gly His Lys Trp Lys
              260                265                     270

Glu Val Arg His Asp Asn Lys Val Thr Trp Leu Val Ser Trp Thr
              275                280                     285

Glu Asn Ile Gln Gly Ser Ile Lys Tyr Ile Met Leu Asn Pro Ser
```

-continued

|     |     |     |     | 290 |     |     |     | 295 |     |     |     | 300 |
|-----|-----|-----|-----|-----|-----|-----|-----|-----|-----|-----|-----|-----|
| Ser | Arg | Ile | Lys | Gly | Glu | Lys | Asp | Trp | Gln | Lys | Tyr | Glu | Thr | Ala |
|     |     |     |     | 305 |     |     |     | 310 |     |     |     | 315 |
| Arg | Arg | Leu | Lys | Lys | Cys | Val | Asp | Lys | Ile | Arg | Asn | Gln | Tyr | Arg |
|     |     |     |     | 320 |     |     |     | 325 |     |     |     | 330 |
| Glu | Asp | Trp | Lys | Ser | Lys | Glu | Met | Lys | Val | Arg | Gln | Arg | Ala | Val |
|     |     |     |     | 335 |     |     |     | 340 |     |     |     | 345 |
| Ala | Leu | Tyr | Phe | Ile | Asp | Lys | Leu | Ala | Leu | Arg | Ala | Gly | Asn | Glu |
|     |     |     |     | 350 |     |     |     | 355 |     |     |     | 360 |
| Lys | Glu | Glu | Gly | Glu | Thr | Ala | Asp | Thr | Val | Gly | Cys | Cys | Ser | Leu |
|     |     |     |     | 365 |     |     |     | 370 |     |     |     | 375 |
| Arg | Val | Glu | His | Ile | Asn | Leu | His | Pro | Glu | Leu | Asp | Gly | Gln | Glu |
|     |     |     |     | 380 |     |     |     | 385 |     |     |     | 390 |
| Tyr | Val | Val | Glu | Phe | Asp | Phe | Leu | Gly | Lys | Asp | Ser | Ile | Arg | Tyr |
|     |     |     |     | 395 |     |     |     | 400 |     |     |     | 405 |
| Tyr | Asn | Lys | Val | Pro | Val | Glu | Lys | Arg | Val | Phe | Lys | Asn | Leu | Gln |
|     |     |     |     | 410 |     |     |     | 415 |     |     |     | 420 |
| Leu | Phe | Met | Glu | Asn | Lys | Gln | Pro | Glu | Asp | Asp | Leu | Phe | Asp | Arg |
|     |     |     |     | 425 |     |     |     | 430 |     |     |     | 435 |
| Leu | Asn | Thr | Gly | Ile | Leu | Asn | Lys | His | Leu | Gln | Asp | Leu | Met | Glu |
|     |     |     |     | 440 |     |     |     | 445 |     |     |     | 450 |
| Gly | Leu | Thr | Ala | Lys | Val | Phe | Arg | Thr | Tyr | Asn | Ala | Ser | Ile | Thr |
|     |     |     |     | 455 |     |     |     | 460 |     |     |     | 465 |
| Leu | Gln | Gln | Gln | Leu | Lys | Glu | Leu | Thr | Ala | Pro | Asp | Glu | Asn | Ile |
|     |     |     |     | 470 |     |     |     | 475 |     |     |     | 480 |
| Pro | Ala | Lys | Ile | Leu | Ser | Tyr | Asn | Arg | Ala | Asn | Arg | Ala | Val | Ala |
|     |     |     |     | 485 |     |     |     | 490 |     |     |     | 495 |
| Ile | Leu | Cys | Asn | His | Gln | Arg | Ala | Pro | Pro | Lys | Thr | Phe | Glu | Lys |
|     |     |     |     | 500 |     |     |     | 505 |     |     |     | 510 |
| Ser | Met | Met | Asn | Leu | Gln | Thr | Lys | Ile | Asp | Ala | Lys | Lys | Glu | Gln |
|     |     |     |     | 515 |     |     |     | 520 |     |     |     | 525 |
| Leu | Ala | Asp | Ala | Arg | Arg | Asp | Leu | Lys | Ser | Ala | Lys | Ala | Asp | Ala |
|     |     |     |     | 530 |     |     |     | 535 |     |     |     | 540 |
| Lys | Val | Met | Lys | Asp | Ala | Lys | Thr | Lys | Lys | Val | Val | Glu | Ser | Lys |
|     |     |     |     | 545 |     |     |     | 550 |     |     |     | 555 |
| Lys | Lys | Ala | Val | Gln | Arg | Leu | Glu | Glu | Gln | Leu | Met | Lys | Leu | Glu |
|     |     |     |     | 560 |     |     |     | 565 |     |     |     | 570 |
| Val | Gln | Ala | Thr | Asp | Arg | Glu | Glu | Asn | Lys | Gln | Ile | Ala | Leu | Gly |
|     |     |     |     | 575 |     |     |     | 580 |     |     |     | 585 |
| Thr | Ser | Lys | Leu | Asn | Tyr | Leu | Asp | Pro | Arg | Ile | Thr | Val | Ala | Trp |
|     |     |     |     | 590 |     |     |     | 595 |     |     |     | 600 |
| Cys | Lys | Lys | Trp | Gly | Val | Pro | Ile | Glu | Lys | Ile | Tyr | Asn | Lys | Thr |
|     |     |     |     | 605 |     |     |     | 610 |     |     |     | 615 |
| Gln | Arg | Glu | Lys | Phe | Ala | Trp | Ala | Ile | Asp | Met | Ala | Asp | Glu | Asp |
|     |     |     |     | 620 |     |     |     | 625 |     |     |     | 630 |
| Tyr | Glu | Phe |     |     |     |     |     |     |     |     |     |     |